US 7,544,188 B2

(12) United States Patent
Edwards et al.

(10) Patent No.: US 7,544,188 B2
(45) Date of Patent: Jun. 9, 2009

(54) MEDICAL INJECTOR

(75) Inventors: Evan T. Edwards, Richmond, VA (US);
Eric S. Edwards, Richmond, VA (US)

(73) Assignee: Intelliject, Inc., Richmond, VA (US)

( * ) Notice: Subject to any disclaimer, the term of this patent is extended or adjusted under 35 U.S.C. 154(b) by 1012 days.

(21) Appl. No.: 10/341,137

(22) Filed: Jan. 13, 2003

(65) Prior Publication Data
US 2003/0100862 A1    May 29, 2003

Related U.S. Application Data

(63) Continuation-in-part of application No. 09/907,609, filed on Jul. 19, 2001, now Pat. No. 6,530,904.

(51) Int. Cl.
*A61M 5/32* (2006.01)
(52) U.S. Cl. ................... 604/197; 604/195
(58) Field of Classification Search .......... 604/185, 604/192, 194, 195, 196, 197, 198, 218, 212, 604/110, 181, 187, 272, 263, 138, 208, 234
See application file for complete search history.

(56) References Cited

U.S. PATENT DOCUMENTS

| | | | |
|---|---|---|---|
| 2,960,087 A | 11/1960 | Uytenbogaart | |
| 3,055,362 A | 9/1962 | Uytenbogaart | |
| 3,115,133 A | 12/1963 | Morando | |
| 3,688,765 A | 9/1972 | Gasaway | |
| 3,768,472 A | 10/1973 | Hodosh et al. | |
| 3,945,379 A | 3/1976 | Pritz et al. | |
| 4,108,177 A | 8/1978 | Pistor | |
| 4,194,505 A * | 3/1980 | Schmitz | 604/138 |
| 4,360,019 A | 11/1982 | Portner et al. | |
| 4,424,057 A | 1/1984 | House | |
| 4,441,629 A | 4/1984 | Mackal | |
| 4,484,910 A | 11/1984 | Sarnoff et al. | |
| 4,563,178 A * | 1/1986 | Santeramo | 604/208 |

(Continued)

FOREIGN PATENT DOCUMENTS

WO    WO 91/04760 A1    4/1991

(Continued)

OTHER PUBLICATIONS

U.S. Appl. No. 11/758,393, Edwards et al.

(Continued)

*Primary Examiner*—Manuel A Mendez
(74) *Attorney, Agent, or Firm*—Cooley Godward Kronish LLP

(57) ABSTRACT

Embodiments of the present invention include a device comprising a substantially planar housing defining a reservoir; a plunger disposed at least partially within said reservoir and movable between a first position and a second position; a liquid dispensing needle coupled to said plunger, said needle comprising a channel in fluid communication with said reservoir, said needle contained within said housing when said plunger is in said first position; and a spring adapted to resist movement of said plunger. It is emphasized that this abstract is provided to comply with the rules requiring an abstract that will allow a searcher or other reader to quickly ascertain the subject matter of the technical disclosure. This abstract is submitted with the understanding that it will not be used to interpret or limit the scope of the invention.

27 Claims, 3 Drawing Sheets

U.S. PATENT DOCUMENTS

| | | |
|---|---|---|
| 4,573,976 A | 3/1986 | Sampson et al. |
| 4,610,666 A | 9/1986 | Pizzino |
| 4,624,660 A | 11/1986 | Mijers et al. |
| 4,643,721 A | 2/1987 | Brunet |
| 4,666,430 A | 5/1987 | Brown et al. |
| 4,673,657 A | 6/1987 | Christian |
| 4,689,042 A | 8/1987 | Sarnoff et al. |
| 4,693,708 A | 9/1987 | Wanderer et al. |
| 4,781,697 A | 11/1988 | Slaughter |
| 4,782,841 A | 11/1988 | Lopez |
| 4,784,652 A | 11/1988 | Wikström |
| 4,874,382 A | 10/1989 | Lindemann et al. |
| 4,894,054 A | 1/1990 | Miskinyar |
| 4,906,235 A | 3/1990 | Roberts |
| 4,915,695 A | 4/1990 | Koobs |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,041,088 A | 8/1991 | Ritson et al. |
| 5,062,603 A | 11/1991 | Smith et al. |
| 5,085,642 A | 2/1992 | Sarnoff et al. |
| 5,092,843 A | 3/1992 | Monroe et al. |
| 5,125,898 A | 6/1992 | Kaufhold, Jr. et al. |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,248,303 A | 9/1993 | Margolin |
| 5,281,198 A | 1/1994 | Haber et al. |
| 5,286,258 A | 2/1994 | Haber et al. |
| 5,298,023 A | 3/1994 | Haber et al. |
| 5,314,412 A | 5/1994 | Rex |
| 5,343,519 A | 8/1994 | Feldman |
| 5,344,407 A * | 9/1994 | Ryan ........................... 604/192 |
| 5,354,284 A | 10/1994 | Haber et al. |
| 5,356,376 A | 10/1994 | Milijasevic et al. |
| 5,380,281 A | 1/1995 | Tomellini et al. |
| 5,383,851 A | 1/1995 | McKinnon, Jr. et al. |
| 5,417,660 A * | 5/1995 | Martin ........................ 604/110 |
| 5,514,135 A | 5/1996 | Earle |
| 5,569,192 A | 10/1996 | van der Wal |
| 5,584,815 A | 12/1996 | Pawelka et al. |
| 5,615,771 A | 4/1997 | Hollister |
| 5,616,132 A | 4/1997 | Newman |
| 5,645,534 A | 7/1997 | Chanoch |
| 5,681,291 A | 10/1997 | Galli |
| 5,695,476 A | 12/1997 | Harris |
| 5,707,365 A | 1/1998 | Haber et al. |
| 5,716,338 A | 2/1998 | Hjertman et al. |
| 5,769,213 A | 6/1998 | Chatterton |
| 5,832,488 A | 11/1998 | Eberhardt |
| 5,837,546 A | 11/1998 | Allen et al. |
| RE35,986 E | 12/1998 | Ritson et al. |
| 5,853,292 A | 12/1998 | Eggert et al. |
| 5,868,713 A | 2/1999 | Klippenstein |
| 5,868,721 A | 2/1999 | Marinacci |
| 5,875,413 A | 2/1999 | Vinci |
| D407,487 S | 3/1999 | Greubel et al. |
| 5,925,021 A | 7/1999 | Castellano et al. |
| 5,941,857 A | 8/1999 | Nguyen et al. |
| 5,964,739 A | 10/1999 | Champ |
| 5,971,953 A | 10/1999 | Bachynsky |
| 6,015,438 A | 1/2000 | Shaw |
| 6,039,713 A | 3/2000 | Botich et al. |
| 6,045,534 A | 4/2000 | Jacobsen et al. |
| 6,063,053 A | 5/2000 | Castellano et al. |
| 6,074,213 A | 6/2000 | Hon |
| 6,086,562 A | 7/2000 | Jacobsen et al. |
| 6,096,002 A | 8/2000 | Landau |
| 6,099,504 A | 8/2000 | Gross et al. |
| 6,102,896 A | 8/2000 | Roser |
| 6,149,626 A | 11/2000 | Rachynsky et al. |
| 6,165,155 A | 12/2000 | Jacobsen et al. |
| 6,179,812 B1 | 1/2001 | Botich et al. |
| 6,193,695 B1 | 2/2001 | Rippstein, Jr. |
| 6,210,359 B1 | 4/2001 | Patel et al. |
| 6,210,369 B1 | 4/2001 | Wilmot et al. |
| 6,221,055 B1 | 4/2001 | Shaw et al. |
| 6,245,046 B1 | 6/2001 | Sibbitt |
| 6,264,629 B1 | 7/2001 | Landau |
| 6,312,412 B1 | 11/2001 | Saied et al. |
| 6,364,866 B1 | 4/2002 | Furr et al. |
| 6,371,939 B2 | 4/2002 | Bergens et al. |
| 6,387,078 B1 | 5/2002 | Gillespie, III |
| 6,413,236 B1 | 7/2002 | Van Dyke |
| 6,425,897 B2 | 7/2002 | Overes et al. |
| 6,428,517 B1 | 8/2002 | Hochman et al. |
| 6,428,528 B2 | 8/2002 | Sadowski |
| 6,475,181 B1 | 11/2002 | Potter et al. |
| 6,478,771 B1 | 11/2002 | Lavi et al. |
| 6,494,863 B1 | 12/2002 | Shaw et al. |
| 6,500,150 B1 | 12/2002 | Gross et al. |
| 6,514,230 B1 | 2/2003 | Munk et al. |
| 6,530,904 B1 * | 3/2003 | Edwards et al. .............. 604/197 |
| 6,535,714 B2 | 3/2003 | Melker et al. |
| 6,544,234 B1 | 4/2003 | Gabriel |
| 6,551,298 B1 | 4/2003 | Zhang |
| 6,569,123 B2 | 5/2003 | Alchas |
| 6,572,584 B1 | 6/2003 | Shaw et al. |
| 6,575,939 B1 | 6/2003 | Brunel |
| 6,585,685 B2 | 7/2003 | Staylor et al. |
| 6,589,158 B2 | 7/2003 | Winkler |
| 6,595,956 B1 | 7/2003 | Gross et al. |
| 6,641,566 B2 | 11/2003 | Douglas et al. |
| 6,645,181 B1 | 11/2003 | Lavi et al. |
| 6,689,093 B2 | 2/2004 | Landau |
| 6,702,778 B2 | 3/2004 | Hill et al. |
| 6,752,781 B2 | 6/2004 | Landau et al. |
| 6,767,336 B1 | 7/2004 | Kaplan |
| 6,770,052 B2 | 8/2004 | Hill et al. |
| 6,783,509 B1 | 8/2004 | Landau et al. |
| 6,786,875 B2 | 9/2004 | Barker et al. |
| 6,793,646 B1 | 9/2004 | Giambattista et al. |
| 6,808,514 B2 | 10/2004 | Schneider et al. |
| 6,830,560 B1 | 12/2004 | Gross et al. |
| 6,936,029 B2 | 8/2005 | Mann et al. |
| 6,953,445 B2 | 10/2005 | Wilmot et al. |
| 6,964,650 B2 | 11/2005 | Alexandre et al. |
| 6,979,316 B1 | 12/2005 | Rubin et al. |
| 2001/0005781 A1 | 6/2001 | Bergens et al. |
| 2002/0074345 A1 | 6/2002 | Schneider et al. |
| 2003/0040717 A1 | 2/2003 | Saulenas et al. |
| 2003/0106824 A1 | 6/2003 | Wilmot et al. |
| 2003/0135388 A1 | 7/2003 | Martucci et al. |
| 2003/0233070 A1 | 12/2003 | De La Serna et al. |
| 2004/0015125 A1 | 1/2004 | Alexandre et al. |
| 2004/0019326 A1 | 1/2004 | Gilbert et al. |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0054327 A1 | 3/2004 | Gillespie, III |
| 2004/0116854 A1 | 6/2004 | Abulhaj et al. |
| 2004/0138611 A1 | 7/2004 | Griffiths et al. |
| 2004/0159364 A1 | 8/2004 | Landau et al. |
| 2004/0220524 A1 | 11/2004 | Sadowski et al. |
| 2004/0249358 A1 | 12/2004 | McWethy et al. |
| 2004/0267204 A1 | 12/2004 | Brustowicz |
| 2005/0033234 A1 | 2/2005 | Sadowski et al. |
| 2005/0090781 A1 | 4/2005 | Baba et al. |
| 2005/0148931 A1 | 7/2005 | Juhasz |
| 2005/0148945 A1 | 7/2005 | Chen |
| 2005/0159705 A1 | 7/2005 | Crawford et al. |
| 2005/0165360 A1 | 7/2005 | Stamp |

| | | |
|---|---|---|
| 2005/0171477 A1 | 8/2005 | Rubin et al. |
| 2005/0267403 A1 | 12/2005 | Landau et al. |
| 2005/0277891 A1 | 12/2005 | Sibbitt |
| 2006/0030819 A1 | 2/2006 | Young et al. |
| 2006/0111666 A1 | 5/2006 | Hommann et al. |
| 2006/0111671 A1 | 5/2006 | Klippenstein |
| 2006/0129090 A1 | 6/2006 | Moberg et al. |
| 2006/0189938 A1 | 8/2006 | Hommann et al. |
| 2006/0200077 A1 | 9/2006 | Righi et al. |
| 2006/0247579 A1 | 11/2006 | Friedman |
| 2007/0088268 A1 | 4/2007 | Edwards et al. |
| 2007/0149925 A1 | 6/2007 | Edwards et al. |

FOREIGN PATENT DOCUMENTS

| | | |
|---|---|---|
| WO | WO 01/93926 A2 | 2/1993 |
| WO | WO 03/095001 A1 | 11/2003 |
| WO | WO 03/097133 A1 | 11/2003 |

OTHER PUBLICATIONS

U.S. Appl. No. 11/692,359, Edwards et al.
U.S. Appl. No. 11/679,331, Edwards et al.
U.S. Appl. No. 11/671,025, Edwards et al.
U.S. Appl. No. 11/621,236, Edwards et al.
U.S. Appl. No. 11/572,148, Edwards et al.
U.S. Appl. No. 11/566,422, Edwards et al.

* cited by examiner

MEDICAL INJECTOR

CROSS-REFERENCE TO RELATED APPLICATIONS

This application is a continuation-in-part of, claims priority to, and incorporates by reference herein in its entirety, U.S. patent application Ser. No. 09/907,609, entitled "Medical Injector," filed Jul. 19, 2001, now U.S. Pat. No. 6,530,904.

BRIEF DESCRIPTION OF THE DRAWINGS

The invention and its wide variety of potential embodiments will be more readily understood through the following detailed description of certain exemplary embodiments, with reference to the accompanying drawings, in which.

DETAILED DESCRIPTION

Certain embodiments of the present invention relate to medical injectors suitable for use with medication that must be injected. Certain embodiments of the present invention relate to a disposable credit card sized injector, suitable for carrying in a wallet or pocket.

Certain embodiments of the present invention comprise a convenient medical injector that can be easy to carry and safe to use, and that can be carried in a pocket or even in a wallet of a user.

Certain embodiments of the present invention comprise a medical injector that can be useful for carrying pharmaceuticals including, but not limited to, epinephrine, insulin medication, anti-nerve agent, snake bite anti-venom, heart medications, allergy medication, and/or various emergency medications such as atropine, lidocaine, and/or morphine.

Certain embodiments of the present invention comprise a medical injector that can include a safety guard, a housing formed of a first casing portion secured to a second casing portion. A pair of hinge portions can provide pivoting motion of a safety guard. A window can be provided to observe the medication fluid stored within the wedge shaped reservoir. The safety guard can protect a pusher bar from accidental actuation.

The pusher bar need not be attached to the housing, and can be free to move relative thereto. The pusher bar can be connected to a column that can pass through an aperture in the stationary bar. The column can be connected directly to a wedge-shaped member that can carry a needle.

A spring means can be disposed between the stationary bar and the pusher bar to resiliently bias the pusher bar into a non-dispensing condition. The wedge-shaped member can be shaped to conform to a wedge-shaped recess formed in the lower casing portion, and the medication fluid can be disposed in the space between the wedge-shaped member and the lower inclined portion of the housing. This space can be a precisely defined volume, containing a precise amount of the medication fluid.

A resilient sleeve can be disposed in a bore formed in the bottom portion of the housing for protecting a needle. The needle can be fixed into the wedge-shaped member. The needle can pass through the rubber or plastic sleeve when the pusher bar is depressed to cause movement of the wedge-shaped member. When the pusher bar is depressed, the needle can penetrate through the resilient sleeve, and can extend beyond the bottom portion of the housing.

Figure 1:
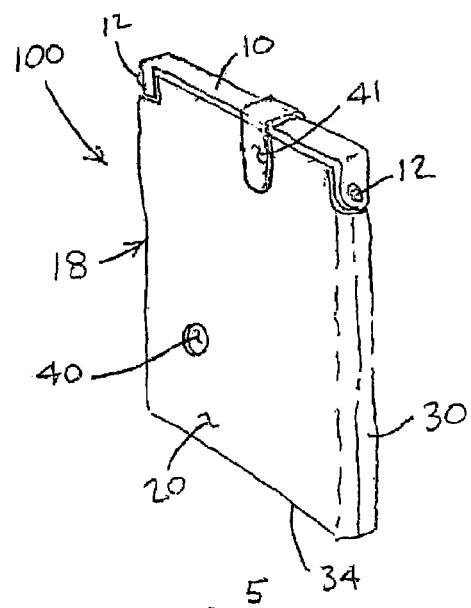
FIG. 1 is a perspective view of an exemplary embodiment of a medical injector according to the present invention.
Figure 2:
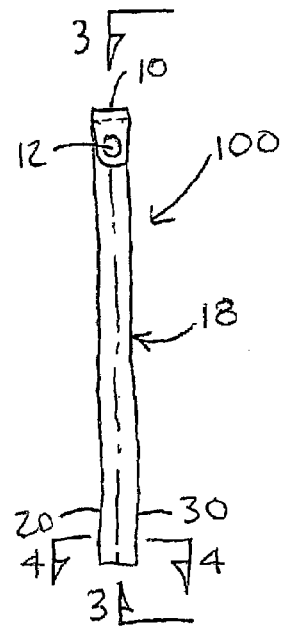
FIG. 2 is a side elevation view of the medical injector of FIG. 1.
Figure 3:
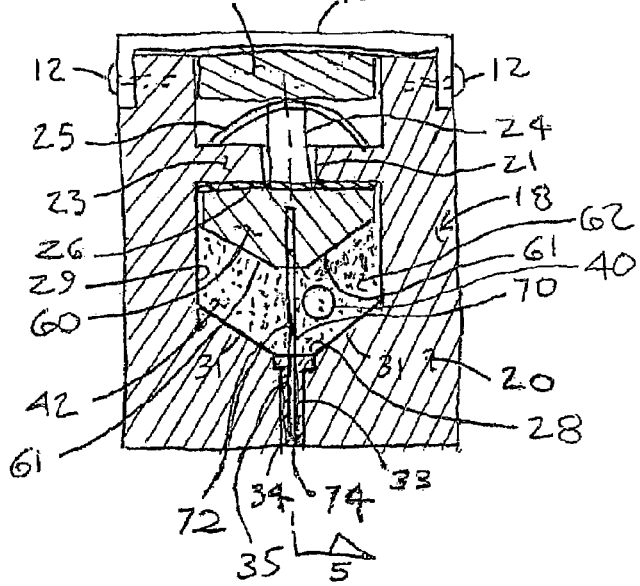
FIG. 3 is a sectional view taken along line 3-3 of FIG. 2.

An exemplary embodiment of a medical injector apparatus 100 is shown in FIGS. 1-7. As shown in FIG. 1, the medical injector apparatus 100 includes a housing 18 having a first casing portion 20, and a second casing portion 30. The first casing portion 20 and the second casing portion 30 are sealed together by any known leak-proof means, such as with adhesive, by heat sealing, by laser bonding, by ultrasonic welding, and/or by fusing, etc. A chamber 28 is formed between the first casing portion 20 and the second casing portion 30, as shown in FIG. 3.

A wedge shaped member or plunger 60 having inclined sides 61, 61 is slidably received within the chamber 28. Although plunger 60 is referred to herein as "wedge shaped member 60" and can have wedge-shaped projection when viewed in a longitudinal cross-section, other embodiments of plunger 60 can have other projections, such as for example, flat, concave, convex, curvilinear, and/or oblique projections. The wedge shaped member 60 may be made of a resilient material, such as rubber, to provide a sliding seal between the interior walls 29 of first casing portion 20 and the second casing portion 30. Alternately, a flexible seal 26 may be secured to the wedge shaped member 60 to provide a sliding liquid tight seal between the wedge shaped member 60 and the interior walls 29 of the chamber 28. A fluid tight seal may also be formed between the column 24 and the stationary bar 23. In an alternative embodiment, any "seal" described herein is not fluid tight, but can leak a relatively small amount of fluid.

A safety guard 10 is pivotally mounted to the housing with a pair of hinge portions 12, 12. The hinge portions 12, 12 provide a pivoting motion of the safety guard 10 about an axis which connects the hinge portions 12, 12. In certain embodiments, hinge portions 12, 12 can be removable from protrusions aligned with that axis and about which hinge portions 12, 12 allow safety guard 10 to rotate. Thus, in certain embodiments, safety guard 10 can be removable from housing 18. In certain alternative embodiments, safety guard 10 can be slideably receivable over and/or slideably removable from housing 18.

The first casing portion 20 preferably has a window 40 therein, which is made of a material which permits inspection of medication fluid 42 inside the medical injector 100, but which does not permit passage of harmful rays there-through. For example, the material of the window 40 should block UV rays. The window 40 can be composed of a glass or plastic material, for example, coated on one side (the side not in contact with the medication fluid 42) to have a UV-blocking coating. For certain medication fluids, it is necessary to block much of the ambient light as well, and therefore the window 40 may be darkened somewhat, similarly to smoked glass.

Alternately, a breakable seal 41 may be used to secure the safety guard 10 to the housing 18, in place over the pusher bar 22 in its raised position. The breakable seal 41 is broken when the safety guard 10 is biased about hinge portions 12,12 to expose the pusher bar 22, indicating that the medical injector apparatus 100 has been used, and should be discarded after use.

FIG. 2 shows the medical injector apparatus 100 of FIG. 1 in a side elevational view. This view also shows the medical injector 100 having the safety guard 10 secured to the housing 18 with opposing hinge portion 12.

FIG. 3 is a sectional view of the medical injector apparatus 100, taken along line 3-3 of FIG. 2. In this view, the wedge shaped member 60, spring means 25 and pusher bar 22 are entirely visible. As seen in FIG. 3, the safety guard 10 located atop the housing 18 protects a pusher bar 22 from accidentally being depressed. The pusher bar 22 is not attached to the housing 18, however, and is free to slidably move between the first casing side 20 and the second casing side 30, against the biasing force of the spring means 25. The spring means 25 may be any known spring means 25, such as a leaf spring, resilient sponge material, coil spring, resilient tab, etc., and all such spring means are intended to be included within the scope of this invention, and the following claims.

The pusher bar 22 is connected to a column 24 which passes through an aperture (such as a bore) in the stationary bar 23. The stationary bar 23 is thus not moved by actuation of the pusher bar 22. The column 24 is connected at one end to the pusher bar 22, and at the opposite end directly to the wedge-shaped member 60. The pusher bar 22, column 24, and the wedge-shaped member 60 therefore move together as a unit when the pusher bar 22 is pushed in a dispensing direction.

A spring means 25 is preferably disposed between the stationary bar 23 and the pusher bar 22, to resiliently bias the pusher bar 22 away from the fluid 42, so as to be in a non-dispensing condition. The wedge-shaped member 60 has inclined sides 61 shaped to conform to the inclined sides 31 of the lower casing 30. The wedge-shaped member 60 may be inclined to allow a small amount of medication to remain in the wedge shaped reservoir 62 when the wedge shaped member 60 is fully depressed, ensuring that air is not injected when the wedge shaped member 60 is fully depressed. The wedge-shaped reservoir 62 is formed within the chamber 28 formed between the first casing side 20, the second casing side 30, the inclined sides 61 of the wedge shaped member 60, and the inclined sides 31 of the lower casing portion 30. The medication fluid 42 is disposed within the wedge shaped reservoir 62 formed between the wedge-shaped member 60 and the housing 18. This space is thus a precisely defined volume, containing a precise amount of the medication fluid 42. Although reservoir 62 is referred to herein as "wedge shaped" and can have wedge-shaped projection when viewed in a longitudinal cross-section, other embodiments of reservoir 62 can have other projections, such as for example, flat, concave, convex, curvilinear, and/or oblique projections.

The bottom portion 34 of the housing 18 also includes a bore 35 extending between the chamber 28 and the bottom portion of the housing 34. The bore 35 is sized to closely receive a resilient sleeve 33 therein. The resilient sleeve 33 is preferably made of rubber or plastic. The resilient sleeve 33 includes a top flange 36, side walls 37 sized to slidably receive the needle 70, and a bottom portion for sealing the needle 70 therein. The needle 70 is secured into the wedge-shaped member 60. The needle 70 passes through the bottom portion 34 of the resilient sleeve 33 when the pusher bar 22 is depressed. This advances the needle beyond the bottom portion 34 of the housing 18, exposing the needle tip 74 for injection of the medication fluid 42, into a user. When the pusher bar 22 is released, the biasing means 25, such as a spring, raises the pusher bar 22, which in turn raises the wedge shaped member 60, which also raises the needle into the protective custody of the resilient sleeve 33.

The needle 70 includes a needle aperture 72 to pass medication fluid 42 into the needle 70 as the wedge shaped member 60 is depressed. The needle aperture 72 is exposed to the medication fluid 42 within the wedge shaped reservoir 62, to permit flow of the fluid 42 through the needle aperture 72, and out through the needle tip 74 when the pusher bar 22 is depressed. For example, the needle 70 can have a slit aperture 72 extending longitudinally, so that even though the needle 70 slit aperture 72 passes partially into the resilient sleeve 33, the needle 70 can continue to receive the fluid 42, as the wedge shaped member 60 is depressed towards the bottom portion 34 of the housing 18. Depression of the pusher bar 22 extends the needle tip 74 beyond the bottom portion 34 of the housing 18 where the needle tip 74 is subsequently injected into the user.

The needle 70, in its retracted position shown in FIG. 3, is preferably slightly shorter than the length of the resilient sleeve 33, so that the needle tip 74 which would be otherwise exposed to the ambient air is instead preferably sealed within the resilient sleeve 33, which may be very snug and self-sealing in the absence of applied pressure on the pusher bar 22.

Figure 4:
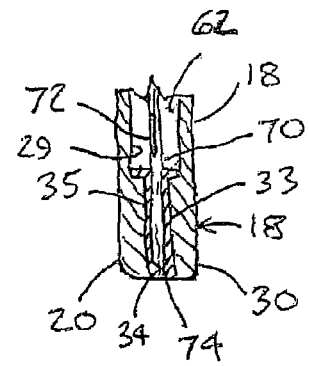
FIG. 4 is a sectional view taken along line 4-4 of FIG. 3.
Figure 6:
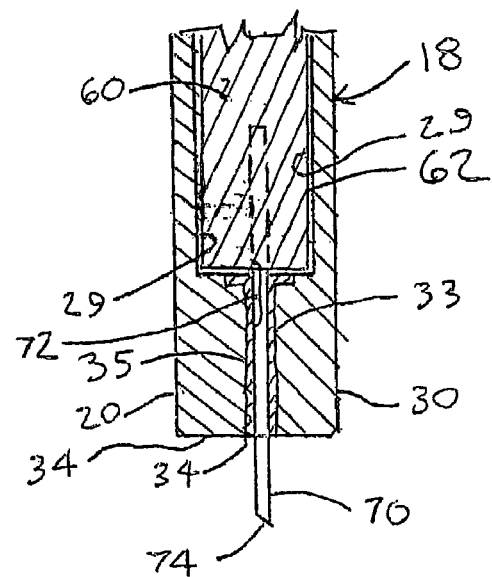
FIG. 6 is a side elevation view of the bottom portion of the medical injector of FIG. 1 wherein a needle portion projects from the bottom wall of a lower casing portion.

FIG. 4 is a sectional view taken along line 4-4 of FIG. 3, showing the needle tip 74 contained within the resilient sleeve 33. In FIG. 6, the needle tip 74 has been actuated so that it projects from the bottom portion 34 of the housing 18. The wedge-shaped member 60 is depressed until the inclined sides 61 abut the inclined sides 31 of the lower casing 30, dispensing a fixed quantity of medication fluid 42 from the wedge shaped reservoir 62 through the needle tip 74 into the user. As previously noted, the inclined sides 61 of the wedge shaped member 60 may be slightly modified to allow some medication to remain in the wedge shaped reservoir 62 when the pusher bar 23 is fully depressed. This ensures that air will not be inadvertently injected with the medication.

To use, the bottom portion 34 of the medical injector apparatus 100 is placed against the user at the desired injection location, breakable seal 41 is removed, and the safety guard 10 is pivoted to expose the pusher bar 22, and the pusher bar 22 is depressed to lower the needle tip 74 beyond the bottom portion 34 of the housing 18. The medication fluid 42 from within the wedge shaped reservoir 62 is forced through the aperture 72 in the needle 70 by the wedge shaped member 60, as the pusher bar 22 is depressed. This may be done directly against the user's skin, or directly through the user's clothing. This avoids the embarrassment of exposing the user's skin at the time of the injection, which is helpful when others are present at the time of the injection. There is a positive tactile feel, when the inclined sides 61 of the wedge shaped member 60 abut the inclined sides 31 of the lower casing 30.

Once the injection has been completed, the pusher bar is released, allowing the spring means 25 to safely reposition the needle tip 74 within the resilient sleeve 33. The safety guard 10 is then pivoted over the pusher bar 22 about hinge portions 12, 12 and secured into place, preventing accidental or inadvertent contact with the needle tip 74 during disposal of the medical injector apparatus 100. The medical injector apparatus 100 disclosed herein is intended to be used once, then discarded, for safety and to avoid possible contamination with a used needle 70.

The wedge-shaped member 60 is movable relative to the housing 18, despite the relatively tight fit, which is necessarily tight in order to form a fluid-tight seal between the wedge-shaped member 60 and the interior walls 29 of the housing 18. A resilient seal 76 may be used between the stationary bar 23 and the wedge shaped member 60 to aid in sealing the medication fluid 42 within the wedge shaped reservoir 62.

Figure 5:
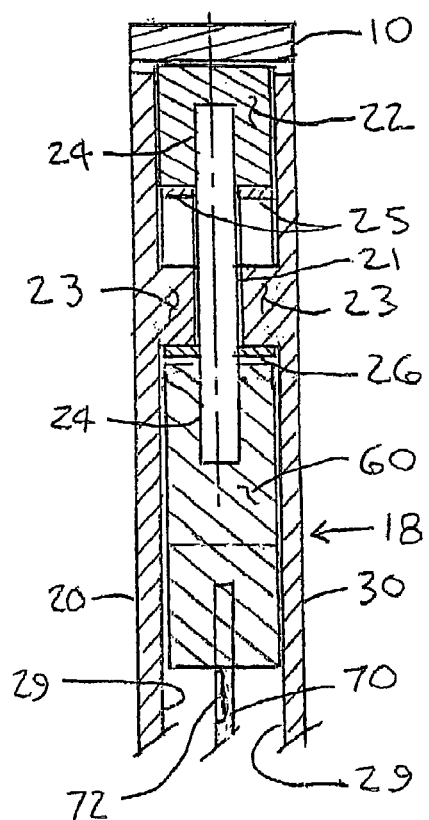
FIG. 5 is an enlarged sectional view of actuator elements and leaf springs, taken along line 5-5 of FIG. 3.

FIG. 5 is an enlarged sectional view of the pusher bar 22, column 24, the stationary bar 23, and at least one spring means 25, taken along line 5-5 of FIG. 3. As seen, column 24 passes through a column aperture 21 in the stationary bar 23. The spring means 25 is preferably disposed on both sides of the column 24, so that, when pressure on the pusher bar 22 is released, the pusher bar 22 is raised, thereby retracting the needle 70 into the housing 18. Thus, the medical injector apparatus 100, once used, presents no accidental sharps hazard during disposal of the medical injector apparatus 100.

FIG. 6 is a side elevational view of the bottom portion 34 of the housing 18 of the medical injector apparatus 100 of FIG. 1. In FIG. 6, the needle tip 74 is shown in its fully extended position, with the needle tip 74 projecting from the bottom portion 34 of the housing 18. As soon as pressure on the pusher bar 22 is released, the needle tip 74 is retracted into the housing 18, ensuring safe disposal of the medical injector apparatus 100 after use.

As seen in FIG. 1, the first casing 20 preferably has a window 40 therein, at a location in alignment with the medication fluid 42 when the pusher bar 22 is not depressed. Thus, the window 40 permits the medication fluid 42 to be viewed through the window 40, enabling the user to determine if the medication fluid 42 has been previously dispensed. The window 40 also permits the user to see if the medication fluid 42 has changed color, or evaporated. Preferably, the window 40 is treated to provide UV resistance, when light sensitive or UV sensitive medication fluid 42 is placed within the medical injector apparatus 100.

A seal means 41 may be secured between the safety guard 10 and the housing 18. The seal means 41 is used to secure the safety guard 10 in place over the pusher bar 22, in its raised position. The seal means 41 is broken, biased or removed to enable the safety guard 10 to pivot about hinge portions 12,12 to expose the pusher bar 22. When the seal means 41 is broken, biased or removed, it is apparent that the medical injector apparatus 100 has been used, and should not be reused. When the safety guard 10 is returned to its protective position over the pusher bar 22, there is no danger of accidentally or inadvertently depressing the pusher bar 22. This ensures that the needle 70 will remain above the lower casing 30. The seal means 41 may be any known type seal, such as an adhesive strip used to secure medication within a container, prior to use.

The safety guard 10 can be adapted to snap lock in place in a manner well known in the art to further protect the pusher bar 22 from being accidentally depressed after use.

The length and width of the housing 18 is preferably sized to be similar to the length and width of a credit card (not shown), and the thickness of the housing 18 is sized to be less than one inch, for ease of transport and storage.

Figure 7:
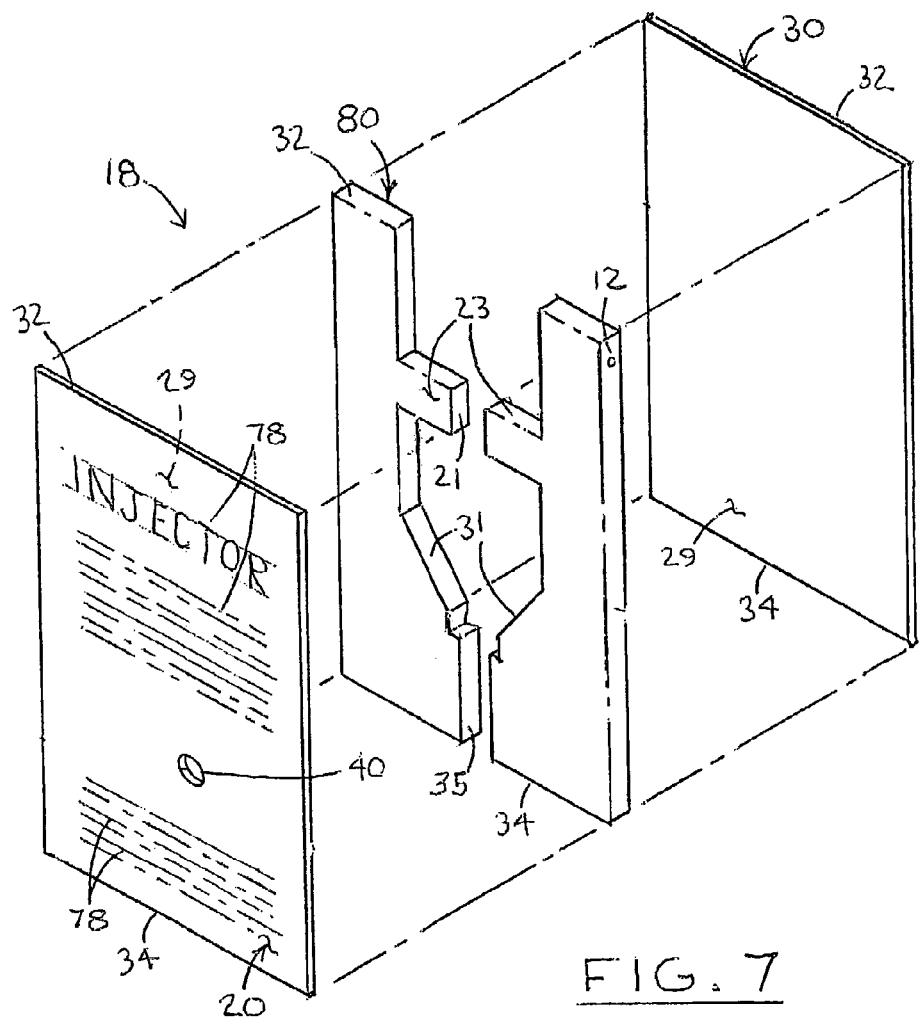
FIG. 7 is an exploded view of an exemplary medical injector apparatus, showing a first casing side, a central housing member and a second casing side, which are secured together to form the medical injector apparatus housing.

The housing 18 may be adapted to comprise a central housing member 80, with the central housing member 80 shaped to provide a wedge shaped reservoir 62 located beneath a stationary bar 23, as shown in FIG. 7. In this adaptation, the first casing side 20 is secured to a one side of the central housing member 80, and the second casing side 30 secured to the opposite side of the central housing member 80. The first and second casing sides 20, 30 enclosing the wedge shaped reservoir 62 therebetween.

Indicia 78 is positioned on at least one of the first casing side 20 and the second casing side 30. The indicia 78 preferably includes information relating to the type of medication fluid 42 stored within the medical injector apparatus 100, and instructions relating to the use and disposal of the medical injector apparatus 100.

The invention being thus described in the form of a preferred embodiment, it will be evident that the invention may be varied in many ways. Such variations are not to be regarded as a departure from the spirit and scope of the invention and all such modifications are intended to be included within the scope of the claims.

What is claimed is:

1. A device, comprising:
   a housing including a planar side wall defining a portion of a boundary of a medicament reservoir having a substantially rectangular cross-sectional shape within a plane substantially normal to a longitudinal axis of a liquid dispensing needle;
   a plunger disposed at least partially within said medicament reservoir and movable between a first position and a second position;
   a liquid dispensing needle coupled to said plunger, said needle including a channel configured to be in fluid communication with said medicament reservoir, said needle contained within said housing when said plunger is in said first position, at least a portion of said needle disposed outside of the housing when said plunger is in said second position; and
   a spring disposed within the housing, the spring configured to bias the plunger.

2. The device of claim 1, further comprising an actuator attached to said plunger.

3. The device of claim 1, wherein said housing is substantially rectangular and has a width and a length approximating that of a credit card.

4. The device of claim 1, wherein said housing has a thickness of less than 1 inch.

5. The device of claim 1, wherein said spring is adapted to resist movement of said plunger toward said second position.

6. The device of claim 1, further comprising a seal adjacent said medicament reservoir and penetrable by said liquid dispensing needle when said liquid dispensing needle is moved from said first position to said second position.

7. The device of claim 1, further comprising a guard adapted to prevent movement of said plunger from said first position toward said second position.

8. The device of claim 1, further comprising an actuator attached to said plunger and a guard adapted to at least partially obstruct access to said actuator.

9. The device of claim 1, further comprising a viewing window in said housing adjacent said medicament reservoir.

10. The device of claim 1, further comprising an actuator coupled to the plunger, the spring being disposed between an internal surface of the housing and the actuator.

11. A device, comprising:
    a housing including a first substantially planar side wall and a second substantially planar sidewall, the first side wall and the second side wall collectively defining a medicament reservoir, the first side wall and the second side wall spaced apart by less than one inch;
    a plunger disposed at least partially within said medicament reservoir and movable between a first position and a second position;
    a liquid dispensing needle coupled to the plunger, the needle configured to be placed in fluid communication with said medicament reservoir, said needle contained within said housing when said plunger is in said first position, at least a portion of said needle disposed outside of the housing when said plunger is in said second position; and
a spring adapted to bias said plunger.

12. The device of claim 11, wherein said housing is substantially rectangular and has a width and a length approximating that of a credit card.

13. The device of claim 11, wherein said spring is adapted to bias said plunger toward said first position.

14. The device of claim 11, wherein said spring is adapted to bias said plunger away from said second position.

15. The device of 11, wherein the medicament reservoir has a substantially rectangular cross-sectional shape within a plane substantially normal to a longitudinal axis of the liquid dispensing needle.

16. The device of claim 11, wherein a distal end of the needle is disposed within an opening defined by the housing when the plunger is in the first position, the distal end of the needle disposed outside of the housing when the plunger is in the second position.

17. A device comprising:
a housing having a first substantially planar side wall and a second substantially planar sidewall, the first side wall and the second side wall collectively defining a medicament reservoir, a length of said housing approximating a length of a credit card;
a member disposed within the medicament reservoir, said member fixedly connected to a needle, said member adapted to move a tip of said needle from a first position within said housing to a second position outside of said housing, a portion of said member in contact with a fluid medication, said member adapted to cause the fluid medication to pass through said needle when said member moves; and
a spring adapted to automatically bias the needle.

18. The device of claim 17, further comprising:
a safety guard adapted to prevent a movement of said member when said safety guard is sealed to said housing.

19. The device of claim 17, further comprising:
a pair of hinge portions adapted to provide pivot motion of a safety guard, the safety guard adapted to prevent motion of said member when the safety guard is breakably sealed to said housing.

20. The device of claim 17, further comprising:
an actuator attached to a column, the column connected directly to said member.

21. The device of claim 17, further comprising:
a resilient sleeve disposed in said housing, said resilient sleeve adapted to protect said tip of said needle when the needle is in the first position.

22. The device of claim 17, further comprising:
a flexible seal secured to said member, said flexible seal adapted to provide a slideable seal between said member and a chamber adapted to hold the fluid medication.

23. The device of claim 17, further comprising:
a seal means for securing a safety guard on said housing.

24. The device of claim 17, further comprising:
an indicia adapted to comprise printed information regarding the fluid medication.

25. The device of claim 17, wherein said housing includes a window adapted for inspection of the fluid medication.

26. The device of claim 17, wherein said housing includes a window adapted for inspection of the fluid medication, wherein the window is adapted to block UV rays.

27. The device of claim 17, wherein the fluid medication is epinephrine.

* * * * *